United States Patent [19]
Colca

[11] Patent Number: 5,929,101
[45] Date of Patent: Jul. 27, 1999

[54] USE OF INSULIN SENSITIZING AGENTS TO TREAT HYPERTENSION

[75] Inventor: Jerry R. Colca, Kalamazoo, Mich.

[73] Assignee: Pharmacia & Upjohn Company, Kalamazoo, Mich.

[21] Appl. No.: 08/963,734

[22] Filed: Nov. 4, 1997

Related U.S. Application Data

[62] Division of application No. 08/320,019, Oct. 7, 1994, Pat. No. 5,719,188, which is a division of application No. 08/052,216, Apr. 22, 1993, Pat. No. 5,356,913, which is a continuation of application No. 07/919,515, Jul. 24, 1992, abandoned, which is a continuation of application No. PCT/US91/00348, Jan. 23, 1991, which is a continuation-in-part of application No. 07/478,090, Feb. 9, 1990, abandoned.

[51] Int. Cl.$^6$ .................. A61K 31/425; A61K 31/35; A61K 31/135; A61K 31/41
[52] U.S. Cl. .................. 514/369; 514/460; 514/646; 514/653; 514/342; 514/365; 514/866
[58] Field of Search ...................... 514/369, 460

[56] References Cited

U.S. PATENT DOCUMENTS

| | | |
|---|---|---|
| 3,542,927 | 11/1970 | McManus . |
| 4,287,200 | 9/1981 | Kawamatsu .............................. 424/270 |
| 4,382,958 | 5/1983 | Duckworth . |
| 4,572,912 | 2/1986 | Yoshioka .................................. 514/369 |
| 4,687,777 | 8/1987 | Meguro ..................................... 514/342 |
| 5,053,420 | 10/1991 | Pershadsingh ........................... 514/369 |

FOREIGN PATENT DOCUMENTS

| | | |
|---|---|---|
| 006 735 | 1/1980 | European Pat. Off. . |
| 008 203 | 2/1980 | European Pat. Off. . |
| 142102 | 5/1985 | European Pat. Off. . |
| 146392 | 6/1985 | European Pat. Off. . |
| 166 183 | 1/1986 | European Pat. Off. . |
| 193 256 | 9/1986 | European Pat. Off. . |
| 283 369 | 9/1988 | European Pat. Off. . |
| 356 214 | 2/1990 | European Pat. Off. . |
| 56-7181 | 6/1981 | Japan . |
| 2 188 234 | 9/1987 | United Kingdom . |

OTHER PUBLICATIONS

Pereda, et al., Am. J. Physiol., 202(2):249–252 (1962).
Ferrannini, et al., New Engl. J. of Med., 317:350–359 (1987).
Bravo, et al., Am. J. Hypertension, 2(12):339S–344S (1989).
Modan, et al., J. Clin. Invest., 75:809–817 (1985).
Shen, et al., J. Clin. Endocrinology and Metalolism, 66:580–583 (1988).
Zavaroni, et al., New Engl. J. of Med., 320(11):702–706 (1989).
Reaven, et al., Lancet, 2:435–436 (1987).
Krotkiewski, et al., Metabolism, 28(6):650–658 (1979).
Reaven, et al., Hypertension, 12(2):129–132 (1988).
Carretta, et al., Hypertension, 7(6):S196–S197 (1989).
Lucas, et al., Hypertension, 7(5):702–706 (1985).
Manicardi, et al., J. Clin. Endocrinology & Metabolism, 62:1302–1304 (1986).
Reaven, et al., Hypertension, 14(2):117–120 (1989).
Tedde, et al., Am. J. Hypertension, 2:163–170 (1989).
Landsberg, Yale Journal of Biology and Medicine, 62:511–519 (1989).
Rose, et al., Hypertension, 8(9):793–800 (1986).
Berglund, et al., Hypertension, 4(5):692–696 (1982).
MacMahan, et al., Lancet, pp. 1233–1236 (1985).
Sowers, et al., Hypertension, 4:686–691 (1982).
Rocchini, et al., Hypertension, 13(6):922–928 (1989).
Nobels, et al., Netherlands J. of Med., 35:295–302 (1989).
Krieger, D.R. and Landsberg, L., Am. J. Hypertension, 1:84–90 (1988).
Connacher, et al., Brit. Med. J., 296:1217–1220 (1988).
Chang, et al., Diabetes, 32:830–838 (1983).
Chang, et al., Diabetes, 32:839–845 (1983).
Pedersen, et al., Diabetic Medicine, 6:249–256 (1989).
Challis, et al., Biochemical and Biophysical Research Comm., 128(2):928–935 (1985).
Rochet, et al., Am. J. Physiol. (Endocrinol. Metab. 18), E101–E109 (1988).
Anderson, et al., Am. J. Gastroenterol., 81:907–919 (1986).
Jimenez, et al., J. Clin. Endocrinol. Metab., 64:661–668 (1987).
Kurtz, et al., Hypertension, 13:896–901 (1989).
Kaplan, et al., Arch. Intern. Med., 149:1514–1520 (1989).
Landsberg, et al., Quarterly J. Medicine, New Series 01. No. 230, 1081–1090, Dec. 1980 (Reference not provided at this time).
Diabetes, vol. 35 Supplement 1, published 1986, p. 66, M.V. Sennitt, et al., Abstract No. 262; and M.A. Cawthorne, et al., Abstract No. 263.

*Primary Examiner*—Theodore J. Criares
*Attorney, Agent, or Firm*—Lawrence T. Welch; Ruth H. Newtson

[57] ABSTRACT

The present invention provides a method for treatin hypertension in insulin resistant patients comprising the administration of an insulin sensitizing agent, particularly ciglitazone or pioglitazone.

1 Claim, No Drawings

USE OF INSULIN SENSITIZING AGENTS TO TREAT HYPERTENSION

CROSS REFERENCE TO RELATED PATENT APPLICATIONS

This application is a division of U.S. Ser. No. 08/320,019, filed 7 Oct. 1994, now U.S. Pat. No. 5,719,188; which was a division application of U.S. Ser. No. 08/052,216, filed 22 Apr. 1993, now U.S. Pat. No. 5,356,913, which was a file wrapper continuation of U.S. Ser. No. 07/919,515, filed 24 Jul. 1992, now abandoned; which was a continuation of the international application PCT/US91/00348, filed 23 Jan. 1991, which was a continuation-in-part of U.S. Ser. No. 07/478,090, filed 9 Feb. 1990, now abandoned.

BACKGROUND

The present invention provides a new use of known pharmaceutical compounds. In particular, the present invention provides for the treatment of hypertension with certain insulin sensitizing agents such as thiazolidinedione derivatives. These compounds are previously known for the treatment of diabetes.

The fact that there was a relationship between circulating insulin and hypertension has been frequently discussed in the literature. Thus, for example, Pereda, et al, Am. J. Physiol. 202 (2): 249–252 (1962) noted an increase in blood pressure in dogs due to the administration of insulin. DeFronzo, Diabetologia 21: 165–171 (1981) attributed this increase in hypertension to the effect of insulin on renal sodium retention which expanded the vascular volume, while Rowe, et al, Diabetes 30:219–225 (March 1981) attributed it to the increased activity of the sympathetic nervous system. Other studies have suggested that hyperinsulinemia as the result of insulin resistance is associated with hypertension. This is attributed to the fact that obesity is known to be associated with insulin resistance and it is a commonly held view that hyperinsulinemia in obesity is a major factor responsible for hypertension. See, e.g., Modan, et al, J. Clin. Invest. 75:809–817 (March 1985). Patients with essential hypertension have been reported to have insulin resistance. Ferrannini, et al, N. Eng. J. Med. 317:350–7 (1987). In the last study a measure of insulin resistance was reported to directly correlate with arterial blood pressure. In patients with a functional endocrine pancreas, insulin resistance also correlates directly with circulating insulin levels.

Ciglitazone is characteristic of a new class of thiazolidine antidiabetic agents which lower blood glucose in animal models of noninsulin diabetes mellitus (NIDDM), while actually reducing circulating concentrations of insulin. This is believed to be accomplished by improving the responsiveness of the peripheral tissues to insulin. See, e.g., Chang, et al, Diabetes 32:830–838 (September 1983).

Because of the high association between diabetes, obesity, and hypertension, and the increase in risk of heart attack in patients exhibiting both diabetes and hypertension (see, e.g., Tzagournis, Am. J. Med., 86 (suppl 1B):50–54 (1989)), what is needed in the art is an agent which will treat both diabetes and hypertension.

INFORMATION DISCLOSURE

Thiazolidine derivatives useful for the treatment of diabetes are described in U.S. Pat. Nos. 4,287,200; 4,687,777; and 4,572,912. Their effect on insulin resistance are described, e.g., Chang, et al, Diabetes 32: 839–845 (1983) and Chang, et al, Diabetes 32:830–838 (1983). The association between circulating insulin and hypertension has been discussed in the literature, as described above.

SUMMARY OF THE INVENTION

The present invention particularly provides a method for treating or preventing hypertension in an insulin-resistant patient comprising the administration of an insulin sensitizing compound to said patient in an amount effective to treat or prevent hypertension. Also provided are specific insulin sensitizing agents for use in this method including thiazolidinediones such as ciglitazone, pioglitazone, and CS 045, metformin, certain indole amines and thermogenic beta agonists.

Surprisingly and unexpectedly, the present invention provides a class of agents useful to treat insulin resistant patients; these agents have an especially good effect in the lowering of blood pressure in said patients.

By insulin sensitizing agent is meant any agent which will lower blood glucose levels by increasing the responsiveness of the tissues to insulin.

By patients susceptible to insulin resistant hypertension is meant a patient who exhibits insulin resistance and is therefore likely to exhibit hypertension. Such patients are well known and readily determinable by a physician of ordinary skill in the art.

By treatment is meant any lowering of blood pressure caused by insulin resistance and/or high circulating insulin levels. By prevention is meant partial to total avoidance of hypertension in insulin resistant patients, depending on the severity of the disease.

The thiazolidinediones are particularly useful in the present invention and are made by the methods described in U.S. Pat. Nos. 4,287,200; 4,687,777; and 4,572,912, which are expressly incorporated by reference herein. The dosage forms and modes of administration described therein are also useful for carrying out the method of the present invention. More specific dose ranges are set out below.

Thermogenic beta agonists are a well known class of antidiabetic agents, exemplified by, e.g., compounds BRL 26,830 (see Biochemica and Biophysica Research Comm. 128:928–935 (1985); and BRL 35,135 (R*,R*)-(+)-methyl)-4-[2-{2-hydroxy-2-(3-chlorophenyl)ethylamino}propyl] phenoxyacetate hydrobromide] Diabetes, Vol. 35: Abstract No. 262 and 263, 1986) being developed by SmithKline-Beecham. Metformin is described, e.g., in Petersen, et al., Diabetic Medicine 6:249–256 (1989). A class of diabetic indole amines are described in copending application Ser. No. 07/270,551, filed 14 Nov. 1988, and PCT application PCT/US89/04711, filed 27 Oct. 1989.

The preferred compounds of this invention include ciglitazone, (2,4-thiazolidinedione, 5-[[4-[(1-methylcyclohexyl)methoxy]phenyl]methyl]-,(+)- or (+)-5-[p-[(1-methylcyclohexyl)methoxy]benzyl]-2,4-thiazolidinedione); Pioglitazone hydrochloride (5-[[4-[2-(5-ethyl-21-pyridinyl-ethoxy]phenyl]methyl]-, monohydrochloride, (+); (2) (+)-5-[p-[2-(5-ethyl-2-pyridyl)ethoxy]benzyl]-2,4-thiazolidinedione monohydrochloride); and CS 045 (5-(4-((3,4-dihydro-6-hydroxy-2,5,7,8 tetramethyl-2 H-1-benzopyran-2-yl)methoxy)phenyl)methyl)-2,4-thiazolidinedione).

While any convenient route of administration is employed, the preferred thiazolidinedione compounds of the present invention are preferably orally administered to humans to affect insulin sensitization for the purpose of favorably affecting blood pressure. For this purpose, the compounds are administered from 100 micrograms per kg to 6 mg per kg per dose, administered from 1 to 3 times daily. Other routes of administration, such as parenteral (including intravenous, intra-muscular, and intraperitoneal) are also employed. Equipotent doses for the other compounds of this invention and the other routes of administration would thus be employed, and could be readily determined by a physician of ordinary skill.

The exact dose depends on the age, weight, and condition of the patient and the frequency and route of administration. Such variations are within the skill of the practitioner or can readily be determined.

The employment of sound medical therapy requires that the compounds of this invention be employed prophylactically only in cases where the animal or patient is particularly susceptible to the development of hypertension. The conditions and circumstances which increase the susceptibility are readily ascertainable to the ordinary skilled physician and include glucose intolerance, insulin resistance, hyperinsulinemia and obesity.

In the prophylactic use of these compounds, the dose effective for the prevention of hypertension is readily determined by patient response, as discussed above for therapeutic uses, and is, in general, somewhat less than the dose required to treat the disease.

DESCRIPTION OF THE PREFERRED EMBODIMENTS

The present invention is seen more fully by the Example given below.

Example 1

Ciglitazone was tested in the Zucker rat, a well known model of insulin resistant mammals and was shown to lower blood pressure, as described below:

Two groups of 6-week old obese female Zucker (fa/fa) rats, 10 control and 10 experimental, were fed a diet containing: 65% carbohydrate, 18% protein, 5% fat, 5% fiber, 0.1% sodium chloride (NaCl), with the remainder containing water, vitamins and minerals.

The experimental group received the drug (ciglitazone powder) as a 0.05% (w/w) dietary admixture (33 to 58 mg/kg body weight/day, calculated from food intake) for 30 days. The control group did not receive the drug.

The mean arterial pressure (MAP) was measured in the unanesthetized, unrestrained state by indwelling femoral artery catheters attached to a pressure transducer, and blood drawn for measurement of blood glucose and plasma insulin concentrations. The results of the study are set forth in Table 1.

Example 2

The effect of insulin sensitizing compounds in primates was shown as follows. Obese, insulin-resistant Rhesus monkeys were given pioglitazone (1 mg/kg/day, oral gavage) for two weeks. Glucose tolerance was substantially improved in 5 of 6 monkeys. Systolic blood pressure was reduced an average of 16 mmH; mean arterial blood pressure (MAP) was reduced an average of 8.4 mmHg. These data show that improved insulin sensitivity produced by drugs of this type are an effective treatment for lowering blood pressure.

TABLE 1

Effects of Ciglitazone on Mean Arterial Pressure (MAP) and Urine Output

| Measurement | Control | Ciglitazone | Significance[1] |
|---|---|---|---|
| MAP (mm Hg) | 119 ± 2 (n = 9) | 112 ± 4 (n = 6) | p < 0.05[2] |
| Urine Output | 80 ± 5 (n = 9) | 97 ± 8 (n = 6) | p < 0.05[3] |
| Insulin (mU/ml) | 171 ± 20 | 60 ± 9 | |

[1]The data is presented as the mean ± SEM and significance determined with the paired Students' t-test.
[2]The one-tailed t-test was used to compare blood pressure measurements.
[3]The two-tailed t-test was used to compare urine output measurements.

There was no significant difference in body weight or food intake between both groups over the period of the experiment. Because of complications during surgery, one animal was lost from the control group, and 4 from the experimental group.

Ciglitazone significantly lowered blood pressure in the fa/fa Zucker rats.

I claim:

1. A method for treating patients who are not exhibiting diabetes but are exhibiting or are susceptible to insulin-resistant hypertension comprising administering to said patient an effective amount of -5-(4-((3,4-dihydro-6-hydroxy-2,5,7,8 tetramethyl-2 H-1-benzopyran-2-yl) methoxy)-2,4-thiazolidinedione.

* * * * *